United States Patent [19]

Gagne

[11] Patent Number: 5,580,521
[45] Date of Patent: Dec. 3, 1996

[54] METHOD AND APPARATUS FOR DISINFECTING AND STERILIZING HOSPITAL WASTES

[75] Inventor: Donald R. Gagne, Raleigh, N.C.

[73] Assignee: American Sterilizer Company, Erie, Pa.

[21] Appl. No.: 259,577

[22] Filed: Jun. 14, 1994

Related U.S. Application Data

[63] Continuation of Ser. No. 18,491, Feb. 17, 1993.

[51] Int. Cl.[6] .............................. A61L 2/20; A61L 2/04; A61L 11/00
[52] U.S. Cl. .............................. 422/28; 422/21; 422/32; 422/27
[58] Field of Search .............................. 422/21, 26, 27, 422/28, 32, 292; 432/DIG. 18

[56] References Cited

U.S. PATENT DOCUMENTS

| | | | |
|---|---|---|---|
| 2,776,214 | 1/1957 | Lloyd et al. | 426/330.1 |
| 4,051,059 | 9/1977 | Bowing et al. | 424/616 |
| 4,764,351 | 8/1988 | Hennebert et al. | 422/292 |
| 4,797,255 | 1/1989 | Hatanaka et al. | 422/292 |
| 5,078,965 | 1/1992 | Pearson | 422/3 |
| 5,116,574 | 5/1992 | Pearson | 422/3 |
| 5,124,125 | 6/1992 | Brent | 422/21 |
| 5,209,411 | 5/1993 | Dineley et al. | 241/17 |
| 5,320,805 | 6/1994 | Kramer et al. | 422/37 X |

FOREIGN PATENT DOCUMENTS

| | | | |
|---|---|---|---|
| 0277507 | 8/1988 | European Pat. Off. | |
| 2644373 | 9/1990 | France | 422/292 |
| 2550142 | 5/1977 | Germany | 422/292 |
| 2908086 | 9/1980 | Germany | 422/292 |
| 2232594 | 12/1990 | United Kingdom | 422/21 |
| 9001340 | 2/1990 | WIPO | |
| 9105572 | 5/1991 | WIPO | 422/21 |

OTHER PUBLICATIONS

*Hackh's Chemical Dictionary*, 4th edi. Julius Grant, editor, 1969, p. 138.

Block, Seymour S., *Disinfection, Sterilization, and Preservation*, 3ed, 1983, p. 242.

Primary Examiner—Robert J. Warden
Assistant Examiner—E. Leigh Dawson
Attorney, Agent, or Firm—Jones, Day, Reavis & Pogue

[57] ABSTRACT

A method and system of treating medical waste product materials that are contaminated with blood, urine and/or other bodily fluids is disclosed. Disinfecting and sterilizing such materials is accomplished through use of heat to deactivate catalase contained in the medical waste. The waste is then contacted with hydrogen peroxide to sterilize the waste.

27 Claims, 2 Drawing Sheets

METHOD AND APPARATUS FOR DISINFECTING AND STERILIZING HOSPITAL WASTES

This is a continuation of copending application Ser. No. 08/018,491 filed on Feb. 17, 1993.

FIELD OF THE INVENTION

The present invention relates generally to the disinfecting and sterilization of contaminated wastes. More specifically, the present invention relates to contaminated wastes typically associated with medical offices, hospitals and clinics treating either animals or humans where the waste materials are contaminated with blood, urine and/or other bodily fluids containing catalase.

BACKGROUND OF THE INVENTION

Discarding medical waste contaminated with blood, urine and/or other bodily fluids, known as "Red Bag" waste, is extremely expensive due to special handling requirements. Two devices which currently are used to treat such wastes include saturated steam disinfection and are manufactured by ABB Sanitek and GTH Roland, KG. The ABB Sanitek machine combines steam and heat treatment, but complete disinfection is suspect due to limited contact time. Likewise, the machine produced by GTH Roland, KG uses only steam and is not completely effective in disinfecting and sterilizing Red Bag wastes.

The ABB Sanitek and GTH Roland saturated steam disinfection processes entail charging Red Bag waste into a lock chamber where it is moistened by either steam or water vapor, while, or just before being ground up. The ground waste is then passed into a chamber where additional steam is added. In the GTH Roland system, steam is used to maintain the waste at an elevated temperature for a specified time to achieve disinfection. The ABB Sanitek system employs microwave generators to maintain the temperature level, and achieve disinfection. In both processes the waste is held at a specified temperature for a given time and then passed out of the chamber to be disposed of as regular waste. However, due to the limited contact time, and reduced temperature and pressure, sufficient sterility is not achieved by these methods.

Chemical sterilization of such Red Bag wastes is not always possible. The reactions between chemical sterilants and the waste products, such as blood catalase, lack of penetration of the waste materials by the chemical sterilant, and the handling problems associated with such chemical sterilants all present difficulties.

Hospitals have long been waiting for alternative methods for treating and disposing of Red Bag wastes which achieve effective sterility levels and which do not present handling difficulties.

SUMMARY OF INVENTION

It is therefore a main object of the present invention to provide a method of completely-disinfecting and/or sterilizing wastes from hospitals and clinics using a liquid chemical sterilant such as liquid hydrogen peroxide and/or peracetic acid to overcome the above stated problems.

It is another object of the invention to provide a method of disinfecting and/or sterilizing wastes in a device which produces safe waste. In the following discussion sterilization is defined as reducing the population of all indicator organisms (bacteria, fungi, viruses and spores) by at least a factor of $10^{-6}$. Disinfection is defined as reducing the population of all indicator organisms (bacteria, fungi, viruses and spores) by at least a factor of $10^{-3}$.

Additional objects and advantages of the invention will be set forth in part in the description which follows, and in part will be obvious from the description, or may be learned by practice of the invention. The objects and advantages of the invention may be realized and obtained by means of instrumentalities and combinations particularly pointed out in the appended claims.

To achieve these objects and in accordance with the purpose of the invention, the present invention provides a method of disinfecting and/or sterilizing contaminated wastes by deactivating the reactive proteins, e.g. blood, catalase, in the waste by first applying heat to the waste material, and then applying a liquid chemical sterilant such as liquid hydrogen peroxide and/or peracetic acid to the waste. The use of a liquid chemical sterilant such as liquid hydrogen peroxide and/or peracetic acid allows penetration of the cellulosic and other waste materials, which is then substantially flashed off or vaporized by applying energy to the waste slurry, thereby disinfecting and/or sterilizing the waste material.

The present invention further comprises a system having a container such as a bin or hopper to collect the waste materials, and a first and second set of augers or other means of transporting the medical waste materials between a first and second heat source. While being transported to the heat source, the waste material is injected by a nozzle or other spraying device with a liquid chemical sterilant such as liquid hydrogen peroxide and/or peracetic acid.

DETAILED DESCRIPTION OF THE PREFERRED EMBODIMENT

The present invention overcomes the disadvantages of current sterilization methods and obviates the need to dispose of Red Bag waste separately from usual medical waste products by heating the wastes to inactivate reactive proteins, such as blood catalase, and, hence, prohibiting the decomposition of the hydrogen peroxide or peracetic acid, and using liquid hydrogen peroxide and/or peracetic acid as the sterilant to permit enhanced penetration in the waste material not achievable through use of hydrogen peroxide vapors. Accordingly, this invention permits the disinfection and/or sterilization of waste materials which would otherwise not be possible.

In a first embodiment of the invention, waste materials contaminated with body fluid contaminates containing catalase and cellulosic materials are moistened, shredded and heated to a temperature sufficient to inactivate the catalase within the waste materials, usually of at least 50° C. The waste materials are then injected with liquid hydrogen peroxide and/or peracetic acid, which penetrates the cellulosics in the waste materials, and are heated to vaporize the hydrogen peroxide and/or peracetic acid to remove a substantial portion of the liquid from the waste materials, thereby disinfecting and/or sterilizing the waste materials. The method may further include grinding the waste materials to a small particle size of about 0.2 inches after injecting the waste materials with hydrogen peroxide and/or peracetic acid and then re-injecting the ground waste materials with additional liquid sterilant before finally heating to vaporize the hydrogen peroxide and/or peracetic acid, thereby removing a substantial portion of the liquid.

A more detailed embodiment comprises feeding the medical waste material into a container means such as a bin or hopper where it is sprayed with steam or water by a fluid conduit means. The moistened waste is then reduced in size by feeding it into a shredder which shreds the waste to a specified particle size, typically 0.5 inch. The shredded waste is then transported by conduit means, such as an auger, where additional steam or water can be added and the waste material is heated by any type of heat source, preferably with microwave energy applied by means of generators attached to the auger system. At the end of the first auger, liquid hydrogen peroxide and/or peracetic acid is injected in concentrations of from about 1.5%–70%, preferably from about 6%–50%, and the shredded waste is ground in a second size reduction means to a small particle size, typically less than 0.2 inch. The ground waste is fed into a second auger where additional microwave generators apply sufficient energy to substantially remove the hydrogen peroxide and/or peracetic acid to a level where disinfection and/or sterilization is achieved. When microwaves are used as the heat source the system housing near the microwaves and the transporting means (e.g. augers) must be made of appropriate materials to be compatible with the use of microwaves, for example, certain grades of plastic and ceramics. The material is heated to vaporize the hydrogen peroxide and/or peracetic acid until it is substantially dry, whereupon it can be disposed of as safe waste. The details of the shredder, grinder, microwave generator and the transportation system (in this case the augers) are unimportant and one of ordinary skill could select from many possible designs and suppliers of such equipment.

In another embodiment of the present invention, additional liquid chemical sterilant such as hydrogen peroxide and/or peracetic acid is added when the material is in the second auger.

In yet another embodiment of the present invention the shredding, moistening, the first heating, and injecting with a liquid chemical sterilant such as hydrogen peroxide and/or peracetic acid steps can be combined into one step and performed in one housing structure. In such an approach, only one auger would be required.

BRIEF DESCRIPTION OF THE DRAWINGS

These and other objects of the invention will be more fully described in the following drawings and in which like numerals represent like elements and in which.

DETAILED DESCRIPTION OF THE DRAWINGS

Figure 1:
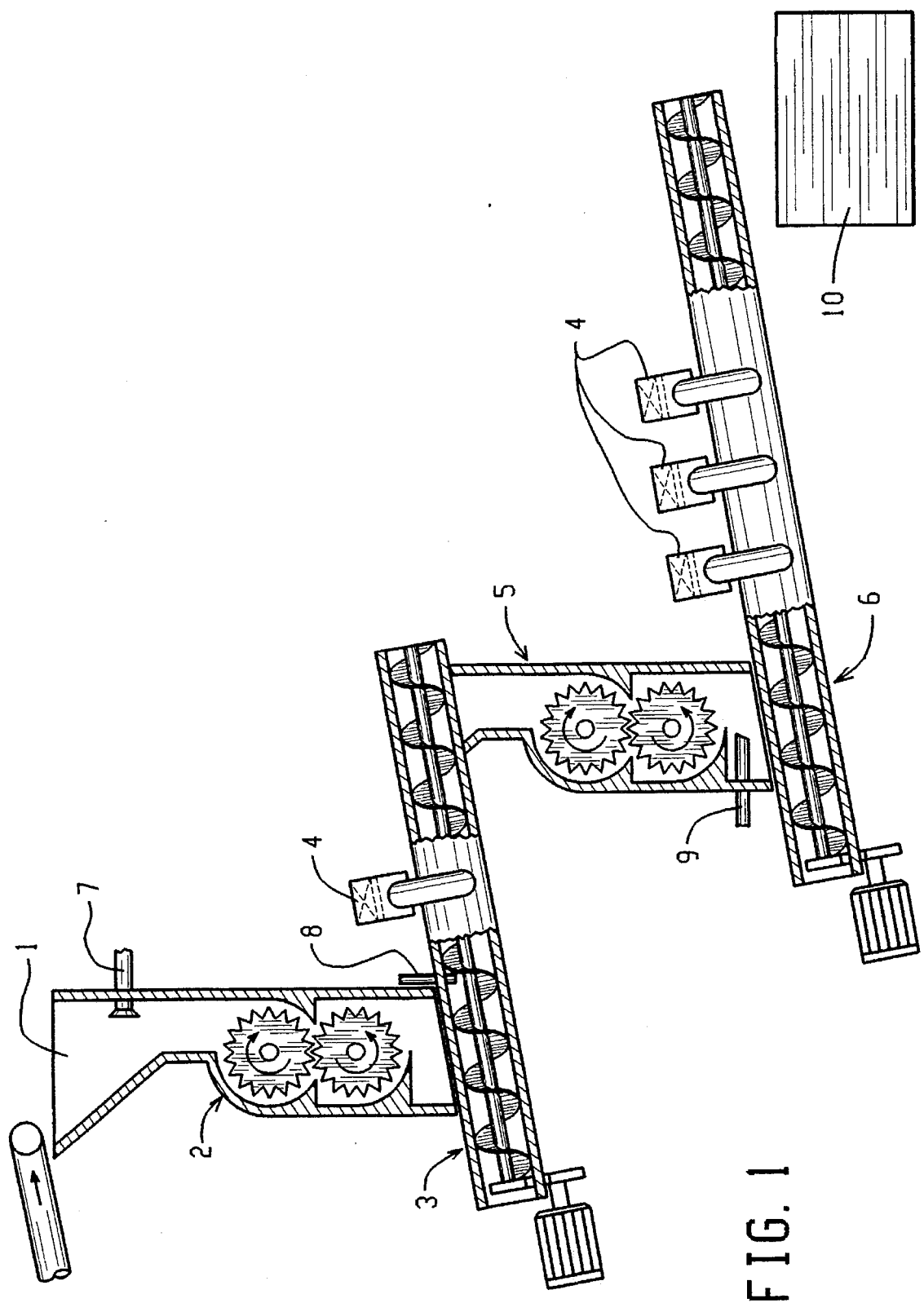
FIG. 1 is a schematic diagram of one embodiment of the present invention.

Reference will now be made in detail to a first embodiment of the invention, which is illustrated in the accompanying drawings as FIG. 1. The decontamination system consists of a bin or hopper (1) where the waste can be deposited and into which steam can be sprayed (7) over the entire contents to achieve uniform moistening of the load. The waste is then fed into a shredder (2) which reduces the particle size to less than ½ inch. The shredder deposits the waste into a transport system which in this case is shown as an auger system (3). The waste materials optionally may be re-moistened with steam (8). Attached to the auger system are microwave generator(s) (4) which provide the energy to heat the shredded waste to achieve inactivation of the catalase. The first auger system empties into a grinder (5) which grinds the shredded waste to a smaller particle size, preferably less than 0.2 inches. As the waste leaves the grinder it is immediately sprayed with a hydrogen peroxide and/or peracetic acid solution which penetrates evenly into the matrix (9). The grinder introduces the waste into the auger transport system (6) which slowly moves the waste towards a standard trash receptacle (10).

Attached to the auger system are microwave generators (4) which apply power to the auger system and thus heat the waste as it moves. Temperature of the system can be measured at various points along the path of the auger in order to monitor the vaporization of the sterilant mixture. Power output of the microwave generators can be adjusted in response to the temperature measurements to make sure the load does not overheat and that the sterilant is substantially removed from the matrix.

Figure 2:
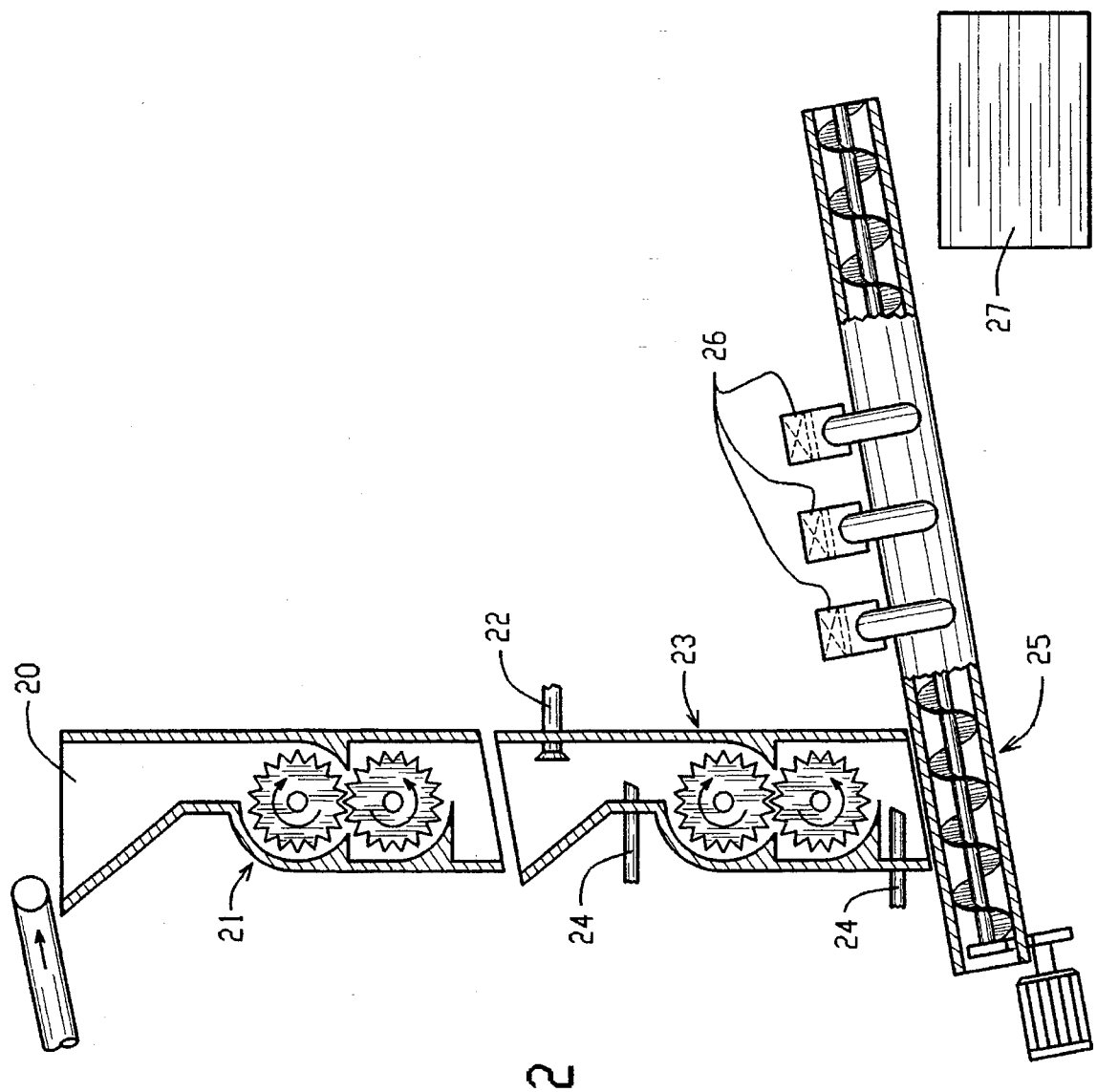
FIG. 2 is a schematic diagram of a second embodiment of the present invention.

Reference will now be made in detail to a second embodiment of the invention, which is illustrated in the accompanying drawings as FIG. 2. The decontaminating system includes a hopper or bin (20) where the contaminated waste can be deposited. The waste is fed into a shredder (21) where it is reduced in size preferably to approximately 0.5 inches. At the exit of the shredder the waste is sprayed with super heated steam in sufficient quantity to inactivate any catalase that may be present in the waste (22). The waste is then immediately deposited within a grinder system (23) which further reduces the waste particle size to below 0.2 inches. A mixture of liquid hydrogen peroxide and/or peracetic acid is sprayed (24) into the load immediately after inactivation is achieved. This can be done just before the grinding system and/or immediately after. A transport system (25) then moves the waste through the field region of a series of microwave generators (26) or other heat source which can be controlled in their output to achieve substantial vaporization of the sterilant and thus achieve disinfection and/or sterilization. The wastes are then deposited in a trash receptacle (27).

EXAMPLES

The following are illustrative examples of the present invention.

Example 1

Spordex spore strips (cellulosics) were inoculated with $2.8 \times 10^6$ Bacillus stearothermophilus. The strips were then covered with 0.5 ml of whole sheeps blood and 6% $H_2O_2$ was added in sufficient quantity to soak the strips. The strips were then exposed to microwave energy for 8 minutes. This process resulted in +8/8 of the strips testing positive for growth after incubation with TSB trypticase soy broth culture media for 24 hours at 55° C.

In comparison, five additional spordex spore strips were then inoculated with $2.8 \times 10^6$ *Bacillus stearothermophilus* and covered with sheeps blood. After application of the sheeps blood additional water was added to the spore strips, which were then briefly microwaved. Six percent $H_2O_2$ was then applied to the samples which were microwaved again until substantially dry. This test resulted in no growth.

Example 2

Twenty grams of ground medical waste were contaminated with 20 ml of sheeps blood containing $10^6$ *Bacillus stearothermophilus* per ml. The waste was moistened and then microwaved for 12 minutes after which 20 ml of 2% $H_2O_2$ were added. The mixture was microwaved for 24 minutes. Five samples of waste withdrawn from the mixture showed no growth when incubated at 55° C. for 7 days in TSB.

What is claimed is:

1. A method of disinfecting a waste material contaminated with a body fluid contaminate, the method comprising the consecutive steps of:

(a) providing a waste material comprising a cellulosic material and further comprising a protein reactive with a sterilant comprising hydrogen peroxide;

(b) applying heat to the waste material in an amount sufficient to inactivate the reactive protein;

(c) applying a liquid chemical sterilant comprising hydrogen peroxide to the waste material in an amount sufficient to penetrate the cellulosic material in the waste material creating a waste slurry; and (d) vaporizing a substantial portion of the hydrogen peroxide in the applied liquid sterilant by applying energy to the waste slurry, whereby the vaporized hydrogen peroxide disinfects the waste material.

2. The method of claim 1, wherein said chemical sterilant also comprises peracetic acid.

3. The method of claim 2, wherein the step of applying a liquid chemical sterilant further comprises the step of using the chemical sterilant having a concentration of between about 1.5%–70%.

4. The method of claim 1 wherein the level of disinfection obtained is sterilization.

5. The method of claim 4, wherein the step of applying a liquid chemical sterilant further comprises the step of using the chemical sterilant having a concentration of between about 6%–50%.

6. The method of claim 1, wherein the step of applying heat to inactivate the reactive protein includes the step of using microwave energy as a heat source.

7. The method of claim 1, wherein the step of vaporizing off the liquid sterilant includes the step of using microwave energy.

8. The method of claim 1 wherein the step of applying heat to inactivate the reactive protein in the waste material includes heating the waste material to at least 50° C.

9. The method of claim 1 wherein the step of applying heat to inactivate the reactive protein in the waste material includes spraying the waste material with super heated steam.

10. A method of disinfecting a waste material contaminated with a body fluid contaminate, the method comprising the steps of:

(a) providing a waste material comprising a protein reactive with a sterilant comprising hydrogen peroxide;

(b) moistening the waste material;

(c) shredding the waste material;

(d) heating the waste material to a temperature sufficient to inactivate the reactive protein within the waste material;

(e) after heating, injecting a liquid chemical sterilant comprising hydrogen peroxide into the moistened heated waste material in an amount sufficient to penetrate the waste material; and (f) after injecting the liquid sterilant, applying energy to the waste material in an amount sufficient to vaporize a substantial portion of the chemical sterilant whereby the vaporized sterilant disinfects the waste material.

11. The method of claim 10, wherein the steps of heating the waste materials includes the step of using microwave energy as a heat source.

12. The method of claim 10, wherein the step of moistening the waste materials further comprises the step of using steam.

13. The method of claim 10, wherein the step of shredding the waste materials further comprises shredding the waste materials to small particle sizes in the range of about 0.2–0.5 inches.

14. The method of claim 10, wherein the liquid chemical sterilant also comprises peracetic acid and wherein the sterilant has a concentration of between about 35–70%.

15. The method of claim 10, wherein the steps of injecting liquid chemical sterilant into the waste materials further comprises using a chemical sterilant having a concentration of between about 3%–70%.

16. The method of claim 10, wherein the steps of injecting liquid chemical sterilant into the waste materials further comprises using a chemical sterilant having a concentration of between about 6%–50%.

17. The method of claim 10, wherein the level of disinfection achieved is sterilization.

18. The method of claim 10 wherein the step of heating said waste material to a temperature sufficient to inactivate the reactive protein within the waste material includes heating the waste material to at least 50° C.

19. The method of claim 10 wherein the step of heating said waste material to a temperature sufficient to inactivate the reactive protein within the waste material includes spraying the waste material with super heated steam.

20. A method of disinfecting a waste material contaminated with a body fluid contaminate, the method comprising the steps of:

(a) providing a waste material comprising a cellulosic material and further comprising a protein reactive with a sterilant comprising hydrogen peroxide;

(b) moistening the waste material;

(c) shredding the waste material;

(d) heating the waste material to a temperature sufficient to inactivate the reactive protein within the waste material;

(e) after heating, injecting a liquid chemical sterilant comprising hydrogen peroxide into the moistened heated waste material in order to penetrate the cellulosic material in the waste material;

(f) grinding the waste material;

(g) injecting an additional amount of liquid chemical sterilant into the ground waste material; and (h) after injecting liquid sterilant, heating the waste material sufficient to vaporize a substantial portion of the chemical sterilant whereby the vaporized sterilant disinfects the waste material.

21. The method of claim 20, wherein in the step of heating the waste material sufficient to vaporize the liquid chemical sterilant further includes heating the waste material until it is substantially dry.

22. The method of claim 20, wherein the chemical sterilant also comprises peracetic acid.

23. The method of claim 20, wherein the step of injecting the chemical sterilant further comprises the step of using the chemical sterilant in a concentration of between about 3%–70%.

24. The method of claim 20, wherein the step of injecting the chemical sterilant further comprises the step of using hydrogen peroxide in a concentration of between about 6%–50%.

25. The method of claim 20, wherein the level of disinfection achieved is sterilization.

26. The method of claim 20 wherein the step of heating the waste material to a temperature sufficient to inactivate the reactive protein within the waste material includes heating the waste material to at least 50° C.

27. The method of claim 20 wherein the step of heating said waste material to a temperature sufficient to inactivate the reactive protein within the waste material includes spraying the waste material with super heated steam.

* * * * *